United States Patent [19]
Roe et al.

[11] Patent Number: 6,060,039
[45] Date of Patent: May 9, 2000

[54] INSECTICIDE RESISTANCE ASSAY

[75] Inventors: R. Michael Roe, Apex; Woodward D. Bailey, Durham; Fred Gould, Raleigh; George G. Kennedy, Apex, all of N.C.

[73] Assignee: North Carolina State University, Raleigh, N.C.

[21] Appl. No.: 09/112,274

[22] Filed: Jul. 8, 1998

[51] Int. Cl.$^7$ .............................. C12Q 1/09; A01N 25/08
[52] U.S. Cl. ............................ 424/9.2; 424/410; 435/29; 426/532
[58] Field of Search .................................. 435/29, 252.31, 435/810; 426/532; 424/9.2, 409, 410; 514/183

[56] References Cited

U.S. PATENT DOCUMENTS

| | | | |
|---|---|---|---|
| 5,141,744 | 8/1992 | Chang et al. | 424/93 |
| 5,246,936 | 9/1993 | Treacy et al. | 514/256 |
| 5,716,831 | 2/1998 | Whalon et al. | 435/19 |
| 5,763,245 | 6/1998 | Greenplate et al. | 435/172.3 |

OTHER PUBLICATIONS

Matsumura, F. Toxicology of Insects. pp. 78–84. Plenum Press, New York. (1975). No month given.

Parrott et al. Feeding and Recovery of Gossypol and Tannin from Tobacco Budworm Larvae. The Southwestern Entomologist 12 (3), pp. 197–204. (Sep. 1987).

Sigma catalog, p. 1447. Sigma Chemical Company. (1989). No month given.

Gould et al., Feeding Behavior and Growth of Heliothis virescens Larvae on Diets Containing *Bacillus thuringiensis* Formulations or Endotoxins. Entomologia Experimentalis et Applicata, 58 (3), pp. 199–210. (Mar. 1991).

Hand et al. Activity of Different Formulations of *Bacillus thuringiensis* on Lepidoptera in Cotton: in Proc. Of Beltwide Cotton Conferences, pp. 908–911. National Cotton Council, Memphis, TN. (Jan. 1996).

Sims et al., Monitoring Strategies for Early Detection of Lepidoptera Resistance to *Bacillus thuringiensis* Insecticidal Proteins. Resistant Pest Management. 9 (1), pp. 21–24. (Summer 1997). No month given.

Van Frankenhuyzen et al.; Specificity of Activated CryIA Proteins From *Bacillus thuringiensis* subsp. kurstaki HD–1 for Defoliating Forest Lepidoptera; Applied and Environmental Microbiology 57:6, 1650–1655 (Jun. 1991).

Cibulsky RJ and Ng SS; Lepton HTK: A Diagnostic Test Kit To Improve Cotton Insect Control, in: *Proceedings Beltwide Cotton Conference*, pp. 889–891. National Cotton Council, Memphis TN. (Jan. 1996).

Gould, Anderson, Jones et al., Initial frequency of alleles for resistance to *Bacillus thuringiensis* toxins in field populations of *Heliothis virescens*, Proc. Natl. Acad. Sci. USA., 94:3519–3523 (Apr. 1997).

Gould, Anderson, Reynolds et al.; Selection and Genetic Analysis of a *Heliothis virescens* (Lepidoptera: Noctuidae) Strain with High Levels of Resistance to *Bacillus thuringiensis* Toxins, J. Econ. Entomol., 88:1545–1559 (Dec. 1995).

Jenkins, Parrott, McCarty et al., Growth and Survival of *Heliothis virescens* (Lepidoptera:Noctuidae) on Transgenic Cotton Containing a Truncated form of the Delta Endotoxin Gene from *Bacillus thuringiensis*, J. Econ. Entomol, 86:181–185 (Feb. 1993).

McGaughy and Whalon, Managing Insect Resistance to *Bacillus thuringiensis* Toxins, Science, 258: 1451–1455 (Nov. 1992).

Ramachandran, Raffa, Miller et al., Behavioral Responses and Sublethal Effects of Spruce Budworm (Lepidoptera: Tortricidae) and Fall Webworm (Lepidoptera: Arctiidae) Larvae to *Bacillus thuringiensis* CrylA(a) Toxin in Diet, Environ–Entomol., 22:197–211 (Feb. 1993).

Rose, Barbhaiya, Roe et al., Cytochrome P450–Associated Insecticide Resistance and the Development of Biochemical Diagnostic Assays in *Heliothis virescens*, Pestic. Biochem. Physiol., 51:178–191 (1995).

Tabashnik B.E., Evolution of Resistance to *Bacillus thuringiensis*, Annu. Rev. Entomol., 39:47–79 (1994).

*Primary Examiner*—Ralph Gitomer
*Assistant Examiner*—Majorie Moran
*Attorney, Agent, or Firm*—Myers Bigel Sibley & Sajovec

[57] ABSTRACT

Methods of assaying insects for pesticide resistance and to identify insect species are based on feeding disruption caused by pesticides such as the biopesticide *Bacillus thuringiensis* toxin (Bt). The assay end-point is feeding disruption, measured by the fecal production of insects exposed to a diagnostic dose of pesticide in a test diet. Pesticide resistance can be assessed at the level of an individual insect or at population levels. Apparatus useful in such assays are described.

17 Claims, 7 Drawing Sheets

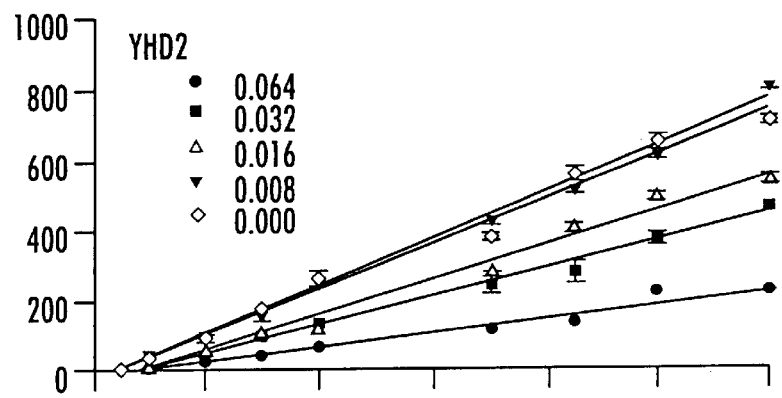
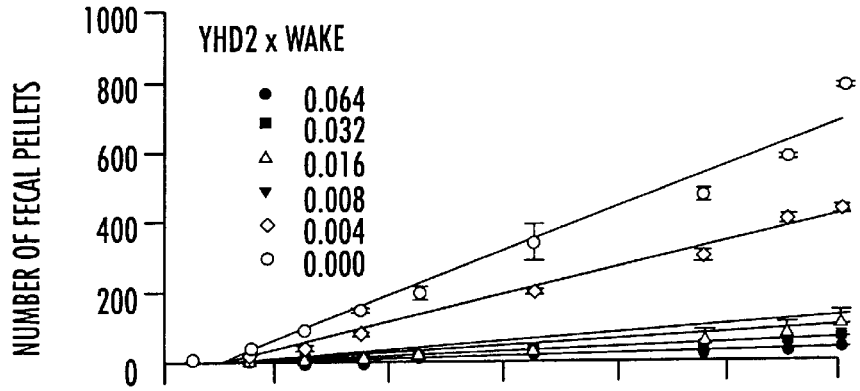
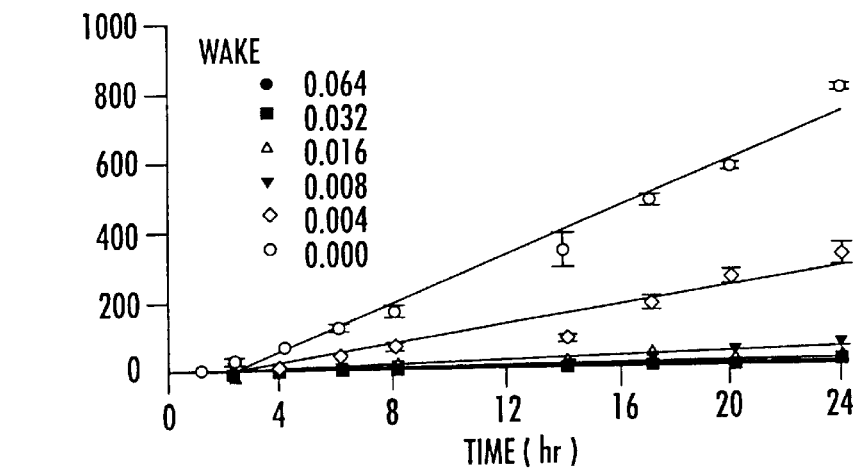
FIG. 1A
FIG. 1B
FIG. 1C

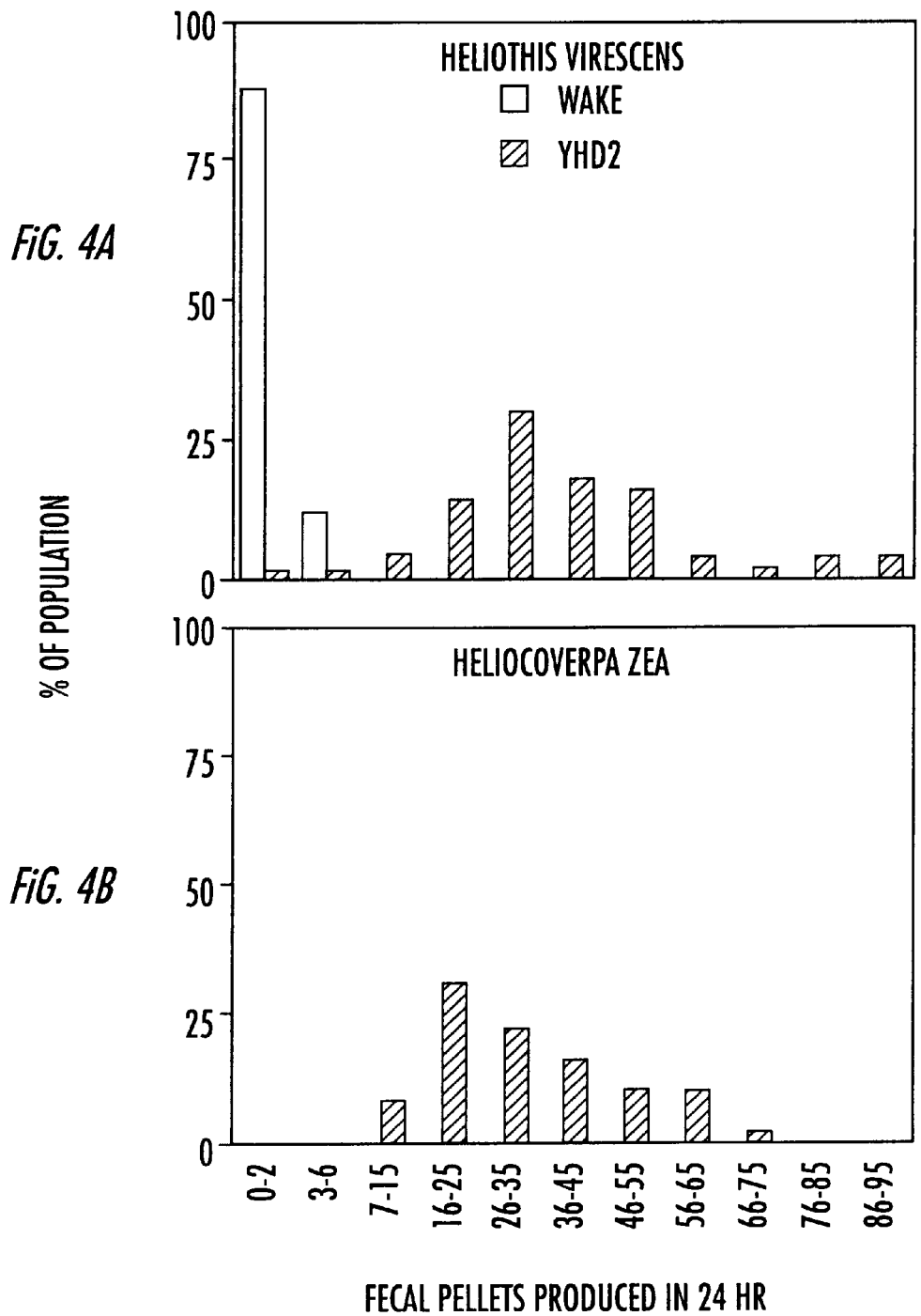

FECAL PELLETS PRODUCED IN 24 HR

INSECTICIDE RESISTANCE ASSAY

This invention was made with Government support under grant USDA NRI-CGP 94-37302-0501. The Government may have certain rights to this invention

FIELD OF THE INVENTION

The present invention relates to methods of testing insects for resistance to pesticides, and in particular to rapid bioassay methods for testing insect resistance to *Bacillus thuringiensis* (Bt) and pyrethroid insecticides. The present invention further relates to assays for the identification of insect species based on resistance or susceptibility to insecticides, and in particular to a method of distinguishing larvae of *Helicoverpa zea* and *Heliothis virescens*.

BACKGROUND OF THE INVENTION

The bacterium *Bacillus thuringiensis* (Bt) contains genes encoding insecticidal proteins. Bt proteins are toxic when ingested by susceptible insect and insect larvae. Bt proteins are used commercially in pesticide formulations, and plants transformed with Bt genes provide transgenic crop plants whose cells produce the insecticidal protein. The Bt gene codes for a protein toxin that attacks the insect midgut, stops feeding and eventually kills susceptible insects. Gill et al., *Annu. Rev. Entomol.* 37:615 (1992); Fischhoff, In *Biotechnology and Integrated Pest Management*, Ed. GJ Persley, pp. 214–227, CAB International, Cambridge, UK.

Several hundred strains of *Bacillus thuringiensis* exist, with considerable specificity toward various groups of insects such as the lepidoptera (butterflies and moths), coleoptera (beetles) and/or diptera (mosquitoes), as well as toward nematodes. Coevolution of insects and Bt has resulted in specificity of the interaction between Bt toxin and the membranes of insect gut cells. The Bt toxin of a particular *B. thuringiensis* strain may bind to the gut of lepidopteran larvae, or only some species of lepidopteran larvae, but not to others. Binding of the protein to the membrane is required for its toxic effects. Thus the Bt toxins have a high specificity for a small number of pest species, while having no significant activity against beneficial insects, wildlife or humans. Lambert and Peferoen, *BioScience*, 42:112 (1992); Gill et al., *Annu. Rev. Entomol.* 37:615 (1992); Meadows, In: *Bacillus thuringiensis, An Environmental Biopesticide: Theory and Practice*, Entwistle et al., Eds., pp. 193–200 (1993).

Formulations of Bt toxin for use as insecticides are known in the art. See, e.g., U.S. Pat. No. 5,747,450; U.S. Pat. No. 5,250,515; U.S. Pat. No. 5,024,837; U.S. Pat. No. 4,797,276; and U.S. Pat. No. 4,713,241.

Plants transformed to carry the Bt gene and express insecticidal proteins are known in the art, and include potato, cotton, tomato, corn, tobacco, lettuce and canola. Krimsky and Wrubel, *Agricultural Biotechnology: An Environmental Outlook*, Tufts University, Department of Urban and Environmental Policy, p. 29 (1993). See also U.S. Pat. No. 5,608,142; U.S. Pat. No. 5,495,071; U.S. Pat. No. 5,349,124; and U.S. Pat. No. 5,254,799. The use of such genetically engineered plants is expected to reduce the use of broad spectrum insecticides. Gasser and Fraley, *Science* 244:1293 (1989).

The use of pesticides results in the selection of individuals resistant to the pesticide, and can lead to the development of pesticide-resistant populations. Resistance to chemical insecticides such as organophosphates, carbamates, spinosyns and pyrethroids are known. Laboratory and field evidence documents that many pests are capable of evolving high levels of resistance to a number of commonly used Bt toxins. Tabashnik, *Annu. Rev. Entomol.* 39:47 (1994); Tabashnik, *J. Econ. Entomol.* 83:1671 (1990); Bauer, *Fla. Ent.* 78:414 (1995); Gould, *Proc. Natl. Acad. Sci. USA* 94:3519 (1997). Resistance may evolve whether the Bt is applied to plants or the plants are genetically engineered to express Bt. The development of resistance to Bt toxin-expressing crops may also result in resistance to commercial formulations of fermented strains of Bt, such as DIPEL® (Abbott Laboratories).

A further concern in the use of plants genetically engineered to express Bt toxins is the difficulty of distinguishing between different pest species that will and will not be controlled by Bt. The presence of a pest in the field that is resistant to Bt indicates the need for supplemental pesticide treatments, whereas no additional treatment is needed if pests are susceptible to Bt. In the case of cotton, transgenic Bt cultivars are exceptionally toxic to most strains of the tobacco budworm *Heliothis virescens* (F.) (Lepidoptera: Noctuidae) (Jenkins et al., *J. Econ. Entomol.* 86:181 (1993)), but are less toxic to the bollworm *Helicoverpa zea* (Boddie) (Lepidoptera:Noctuidae) (Lambert et al., In: *Proceedings Beltwide Cotton Conference*, pp. 931–935, National Cotton Council, Memphis Tenn. (1996)). *H. zea* and *H. virescens* are found in the same geographic areas, and in years when *H. zea* populations are high, larva that are not killed by ingestion of Bt can cause significant damage to cotton. The eggs and young larvae of *H. zea* and *H. virescens* are indistinguishable by simple observation in the field (although adults are readily distinguished visually). Without a test to distinguish among susceptible and resistant species, farmers finding lepidopteran eggs or neonates on cotton cannot rely on Bt cotton for control of lepidopteran pests.

Rapid, reliable methods to distinguish Bt-susceptible from Bt-resistant species, and to detect the development of Bt resistance in populations of insects, are desirable. The methods of the present invention provide a bioassay capable of distinguishing between *H. virescens* and *H. zea*. The present methods can also detect insect resistance to Bt within a species.

SUMMARY OF THE INVENTION

In view of the foregoing, a first aspect of the present invention is a method of detecting, in a plurality of insect larvae that appear to be *H. virescens* larvae, the presence of *H. zea* larvae. Each of the larvae is given access to a test diet containing a predetermined diagnostic amount of *Bacillus thuringiensis* toxin, for a predetermined time, and the amount of feces produced by each of the larvae over the predetermined time is assessed. A larva that produces more than a predetermined diagnostic amount of feces is *H. zea*.

A further aspect of the present invention is a method of detecting, in a plurality of insects, the presence of insects resistant to a pesticide that causes feeding disruption in susceptible insects. Each of the insects is given access to a test diet containing a predetermined diagnostic amount of the insecticide, for a predetermined time, and the amount of feces produced by each of the insects over the predetermined time is assessed. An insect that produces more than a predetermined diagnostic amount of feces is resistant to the pesticide.

A further aspect of the present invention is a method of assessing insects for resistance to a pesticide that causes feeding disruption in susceptible insects. The insects are given access to a test diet containing a predetermined diagnostic amount of the insecticide, for a predetermined time. The amount of feces produced by the insects over the predetermined time is assessed; insects producing more than a predetermined diagnostic amount of feces are resistant to the pesticide.

A further aspect of the present invention is a method of designing an assay to discriminate between an insect type resistant to a pesticide and an insect type susceptible to a pesticide, where the pesticide causes feeding disruption. A plurality of each of the insect types to be tested is obtained, and a dose/response study of the pesticide is conducted using a test diet, to determine a diagnostic dose of the pesticide and a diagnostic feeding period that can distinguish (by the amount of feces produced during the feeding period) the resistant insect type from the susceptible insect type.

A further aspect of the present invention is a method of designing an assay to screen for the development of pesticide resistance in a homogenous population of insects, where said pesticide causes feeding disruption. A plurality of insects from said population is obtained, and a dose/response study of the pesticide in a test diet is conducted to determine a diagnostic dose of the pesticide and a diagnostic feeding period at which a statistically significant decrease in the amount of feces produced by the insects occurs, compared to fecal production by insects on a control diet.

A further aspect of the present invention is a kit for testing insects for resistance to a pesticide that causes feeding disruption. The kit includes at least one container sized to house at least one of the insects being tested, a test diet, and printed instructions setting forth a diagnostic time period and a diagnostic amount of feces that indicates the insects are resistant to the pesticide being tested.

BRIEF DESCRIPTION OF THE DRAWINGS

FIG. 1A graphs the effect of different concentrations of CryIAc on the production of fecal pellets by third instars of the YHD2 strain of the tobacco budworm, *H. virescens*. CryIAc was placed in Trypan Blue diet in concentrations of 0.000 μg/ml diet (solid diamonds); 0.008 μg/ml diet (solid triangles); 0.016 μg/ml diet (open triangles); 0.032 μg/ml diet (squares); and 0.064 μg/ml diet (circles). Each treatment represents the average of three replicates of 15 insects per replicate. Error bars are ±1 S.E., which in most cases does not exceed the size of the graph symbol.

FIG. 1B graphs the effect of different concentrations of CryIAc on the production of fecal pellets by third instars of the YHD2×Wake strain of the tobacco budworm, *H. virescens*. CryIAc was placed in Trypan Blue diet in concentrations of 0.000 μg/ml diet (open circles); 0.004 μg/ml diet (solid diamonds); 0.008 μg/ml diet (solid triangles); 0.016 μg/ml diet (open triangles); 0.032 μg/ml diet (squares); and 0.064 μg/ml diet (solid circles). Each treatment represents the average of three replicates of 15 insects per replicate. Error bars are ±1 S.E., which in most cases does not exceed the size of the graph symbol.

FIG. 1C graphs the effect of different concentrations of CryIAc on the production of fecal pellets by third instars of the Wake strain of the tobacco budworm, *H. virescens*. CryIAc was placed in Trypan Blue diet in concentrations of 0.000 μg/ml diet (open circles); 0.004 μg/ml diet (solid diamonds); 0.008 μg/ml diet (solid triangles); 0.016 μg/ml diet (open triangles); 0.032 μg/ml diet (squares); and 0.064 μg/ml diet (solid circles). Each treatment represents the average of three replicates of 15 insects per replicate. Error bars are ±1 S.E., which in most cases does not exceed the size of the graph symbol. Fecal production was minimal at concentrations >0.004 μg CryIAc/ml diet, preventing separate plots for each data set.

FIG. 4A graphs the percentage of the test population producing blue fecal pellets as neonates in 24 hours on CryIAc-Trypan Blue diet (0.032 μg CryIAc/ml), where shaded bars represent YHD2 larvae and open bars represent Wake larvae. Results were taken from two replicates consisting of 25 insects per replicate for each species and strain.

FIG. 4B graphs the percentage of the test population of *Helicoverpa zea* producing blue fecal pellets as neonates in 24 hours on CryIAc-Trypan Blue diet (0.032 μg CryIAc/ml). Results were taken from two replicates consisting of 25 insects per replicate for each species and strain.

DETAILED DESCRIPTION OF THE INVENTION

Figure 2:
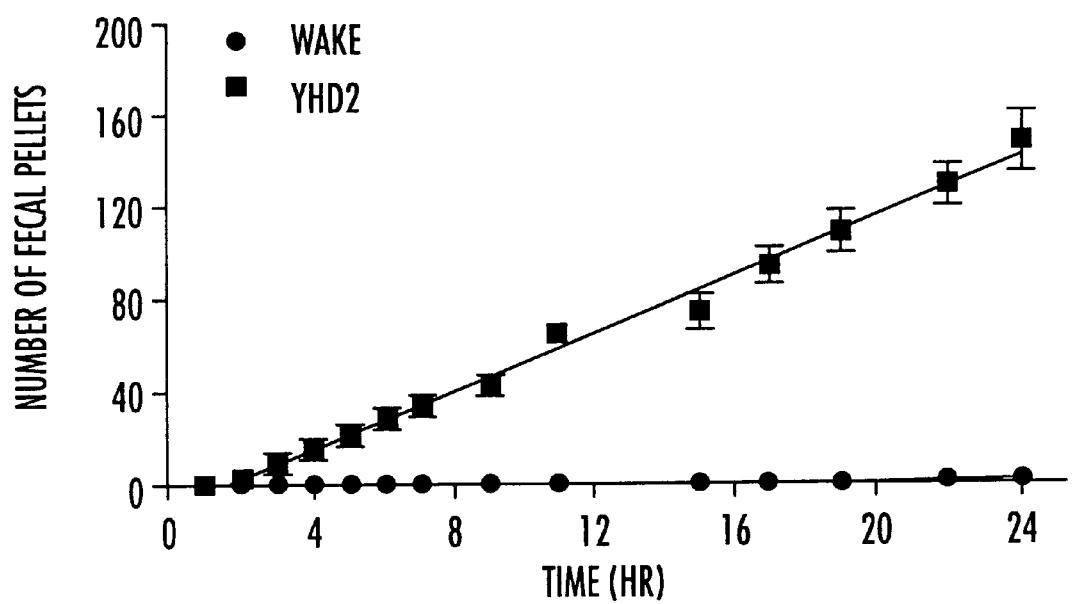
FIG. 2 graphs the effect of 0.032 μg CryIAc/ml of Trypan Blue diet on fecal pellet production by Wake (circles) and YHD2 (squares) third instars previously reared on cotton. Each treatment is the average of three replicates of 15 insects per replicate. Error bars are ±1 S.E., which in most cases does not exceed the size of the graph symbol.

The most common endpoint for assessing Bt susceptibility in lepidopteran larvae has been mortality at 7 to 10 days after treatment. Van Frankenhyzen et al., *Appl. Environ. Microbiol.* 57:1650–1655 (1991) used a 50% reduction in frass production in three days as a measure of toxicity for different Bt toxins against several species of forest pests.

Immunochemical and DNA amplification methods of species identification for *H. zea* and *H. virescens* are known. Cibulsky and Ng, In: *Proceedings Beltwide Cotton Conference*, pp. 889–891, National Cotton Council, Memphis Tenn. (1996); Roehrdanz, R. USDA ARS Report Number 075350; U.S. Pat. No. 5,656,437 (Greenstone). Such methods can be cost-prohibitive and may not be convenient for field use.

An additional method to distinguish *H. virescens* and *H. zea* eggs is described in Cibulsky and Ng, In: *Proceedings Beltwide Cotton Conference*, pp 889–891, National Cotton Council, Memphis Tenn. (1996).

The present pesticide resistance assays and species identification assays are based on feeding disruption caused by pesticides such as the biopesticide *Bacillus thuringiensis* toxin (Bt). The assay end-point is feeding disruption, which is measured by the fecal production of insects exposed to a diagnostic dose of pesticide in a test diet. The test diet preferably also contains a marker compound as an aid in assessing fecal production from the test diet. Resistance can be assessed at the level of an individual insect or at population levels. Where insect larvae are utilized, those that survive the present assay methods can be reared to mature larvae or adults for visual species identification, or for use in immunodiagnostic identification assays if desired.

The present inventors found that both Bt resistant and Bt susceptible third instars of the tobacco budworm (*H. virescens*) produced feces when fed a diet containing Bt, but that the rate of defecation was greatly reduced in susceptible insects. Feces produced by budworms on such diets could be derived from several possible sources, i.e., the Bt-containing test diet; from residual food in the larval digestive system from feeding prior to initiation of the bioassay; or from feeding on extraneous materials such as the cardboard lid of the assay container or egg chorion. To provide a marker for feeding on diet containing Bt toxin, Trypan Blue was incorporated into a standard artificial diet at the rate of 20 mg/ml of diet. Trypan Blue was selected because the blue feces produced by budworms on this diet can be easily distinguished from the brown feces derived from normal artificial diet, from the dark green feces produced by budworms feeding on cotton plants, and from the lightly colored feces produced by neonates feeding on the egg chorion. Insects reared on the Trypan Blue diet produced a distinctive smooth and shiny blue fecal pellet, different in appearance from feces produced by insects feeding on other possible sources.

Using a test diet containing a predetermined amount of Bt and Trypan Blue as a marker for ingestion of the test diet, the present inventors devised an assay to distinguish Bt resistant and Bt susceptible strains of *H. virescens*. The number of fecal pellets containing the marker, produced over a predetermined time period after exposure to a test diet containing a predetermined amount of Bt toxin, is indicative of Bt susceptibility or Bt resistance. The present methods are useful in detecting *H. virescens* larvae with economically significant levels of Bt resistance. The present methods are additionally useful in distinguishing between *Heliothis virescens* (Bt susceptible) and *Helicoverpa zea* (Bt resistant) species.

The present invention provides a method of detecting *H. zea* larvae within a group of larvae that appear to be *H. virescens*. Each larva is given access to a test diet containing a predetermined diagnostic amount of *B. thuringiensis* toxin. The diagnostic amount is previously determined using dose/response studies as outlined in the Examples provided below and knowledge in the art, to determine a dose of toxin and a time period during which *H. zea* larva (resistant to the Bt toxin) produce an amount of feces that is significantly greater than that produced by *H. virescens* (susceptible to Bt toxin) larva. After a larva is given access to the test diet for the predetermined test time, the amount of feces produced during that time is assessed, for example by counting the number of fecal pellets produced. Larvae that produce more than the predetermined diagnostic amount of feces are considered to be *H. zea*. In an exemplary assay, the test diet contains CryIAc *Bacillus thuringiensis* toxin at a concentration of from about 0.030 µg, or from about 0.032 µg, to about 0.035 µg CryIAc/ml diet, and the test time is 24 hours. Larvae producing seven or more fecal pellets are indicated as *H. zea*.

The present invention further provides a method of detecting, in a single test larva or in a plurality of test larvae, resistance to a pesticide known to cause feeding disruption in susceptible insects. Each larva is given access to a test diet (containing a predetermined resistance-diagnostic amount of the insecticide) for a predetermined time. The amount of feces produced by each larva over the test time is then quantified. Any larva producing more than the predetermined diagnostic amount of feces is considered resistant to the pesticide. The resistance-diagnostic amount of insecticide and the test time are previously determined using dose/response assays as described herein, and techniques known in the art. It will be apparent to those skilled in the art that "resistance" is a relative term; an insect that is resistant to a low level of an insecticide may be susceptible to a larger dose.

The present invention further allows one to design an assay to discriminate between an insect type that is resistant to a pesticide and an insect type that is susceptible to a pesticide, where the pesticide is one that causes feeding disruption. As used herein, an 'insect type' may be a species, a subspecies, a particular strain of a species, or a geographic population of a species or subspecies or strain. Multiple larvae of each of the insect types are obtained, and a dose/response study is conducted, using methods described in the Examples below and knowledge in the art. The dose/response study determines a diagnostic dose of the pesticide, and a diagnostic feeding period, whereby the amount of feces produced by the two insect types differ significantly.

The present invention further allows one to design an assay to screen a homogenous population of insects for the development of pesticide resistance, where the pesticide causes feeding disruption. The screening may occur over time or over a geographic area. A homogenous population, as used herein, may refer to a particular species, subspecies or strain of insect, or a geographic population of a particular species, subspecies or strain. Larvae are obtained from the population of insects being tested, and a dose/response study is conducted to determine a resistance-diagnostic dose of said pesticide, and a diagnostic feeding period, during which the amount of feces produced by the larvae decreases significantly, compared to larvae fed on a control diet. Testing of additional subjects over time or over a geographic area can be used to detect the development of increased resistance to the pesticide.

In each of the above methods, the test diet may additionally contain a marker compound that imparts a detectable characteristic to feces produced by the test subject. A preferred marker is the dye Trypan Blue. Additionally, it is preferred that the larva test subjects be starved for a period of time prior to being placed on the test diet, for example, for about an hour.

As used herein, a plurality of insect larvae may refer to a sample of insect larvae taken from a field, or to insect larvae produced by insects obtained from a field. As used herein, giving larvae access to a test diet means that larvae are placed in contact with or in close proximity to the test diet, and the larva are allowed to feed at liberty.

The present invention further provides a kit for testing insect larvae for resistance to a pesticide, where the pesticide causes feeding disruption. The kit contains at least one container of a size sufficient to contain at least one of the test insect larvae during the test period, and contains a test diet with a resistance-diagnostic amount of the pesticide. Printed instructions set forth the diagnostic time period, and the amount of feces that indicates that the test larva is resistant to the pesticide.

The present methods can be used with any insecticide that causes feeding disruption by any means (behavioral or physiological) in susceptible insects, including chemical insecticides and biopesticides such as Bt toxin. Chemical insecticides include pyrethroids (cypermethrin, bifenthrin, cyfluthrin, esfenvalerate, permethrin, tralomethrin, cyhalothrin, zetacypermethrin), carbamates, diamidides, organophosphates, organochlorines, spinosyns and chloronicotinoids.

Pyrethroid-resistant populations of tobacco budworms (*H. virescens*) have been documented in the Southeastern United States. Resistance is typically measured using mortality assays, such as a 'vial test' in which glass vials are coated on the inside with a predetermined dose of insecticide that kills a majority of susceptible moths but not resistant moths. Strains of tobacco budworm resistant to carbamate and organophosphate insecticides are also known. Additionally, strains of cotton bollworm (*Helicoverpa armigera*) resistant to pyrethroid insecticides are known in Australia, and may exhibit cross resistance to several pyrethroids.

The present methods are suitable for use with any insect that is susceptible to, or that is exposed to, an insecticide that causes feeding disruption and reduced fecal output. Such insects include, but are not limited to, the tobacco budworm (*Heliothis virescens*), bollworm or cotton earworm (*Helicoverpa zea*), and diamondback moth (*Plutella xylostella*). Susceptible insects may be monitored for the development of resistance or to assess levels of resistance; the feeding disruption assay may be carried out using larvae or adult insects, as would be apparent to one skilled in the art. As used herein, the term "insect" refers to both larval and adult forms of insects. As used herein, an "insect type" refers to a distinct group of insects that can be characterized by morphological, geographical, or phenotypical characteristics. An insect type may be a species or sub-species, or a geographical variant or isolate of a species.

As used herein, a test diet refers to a diet suitable for the insect(s) being tested, as is known in the art. In the present assays, a predetermined amount of pesticide is provided in the test diet; the amount of pesticide is sufficient to cause a statistically significant difference in fecal output between resistant and susceptible insects (species or strains) over a predetermined time period. The amount of pesticide will vary depending on the pesticide, the insect species, and the time over which feeding is allowed to occur. The amounts of pesticide and the time course of a particular assay may be determined by one skilled in the art using the procedures as taught herein. The same diet, but lacking any pesticide, may be used as a control.

The present test diets preferably also contain a marker substance. As used herein, a marker substance is one that, when ingested by an insect, imparts a detectable characteristic to feces produced by the insect. The detectable characteristic may be color, overall appearance, or a chemically detectable reaction. Preferred markers are dyes that impart a distinct color to fecal pellets; a particularly preferred marker is the dye Trypan Blue. Also useful are pH sensitive dyes, fluorescent dyes, and cytosolic markers of any type.

The present feeding disruption assays are simple and suitable for use by farmers and extension agents. The assay can be conducted on individual insects collected from the field as eggs, larva, neonates or older larvae, and results can be obtained within a short time, such as within 24 hours. Because the feeding disruption test does not result in the death of the insect, insects can subsequently be used for additional diagnostic assays, such as assaying for resistance to chemical insecticides, and/or can be raised to adulthood for visual species identification.

It will be apparent to those skilled in the art that an insect that is resistant to an insecticide at a particular dose may be susceptible to the same insecticide at a higher dose. As used herein, "resistance" and "susceptibility" are not absolute, but refer to survival after exposure to a particular dose of insecticide. Species and strains commonly referred to as "resistant" are those that survive exposure to recommended commercial doses of insecticide. The present assays are useful in detecting the presence of insects in the field that are resistant to recommended doses of commercial insecticides, and are further useful in detecting the level of resistance present in a population or strain of insect, or in comparing the relative resistance of two species or strains. Resistance, as used herein, does not imply that an insect is impervious to all effects of an insecticide, or that a higher dose of the insecticide would not harm the insect.

Accordingly, the present invention provides methods to assess resistance (e.g., determining the response to varying dosages of insecticide in a homogenous population of insects). The present invention further provides methods for typing species or strains of insects based on previously determined resistance profiles (e.g., typing larvae collected from the field to distinguish between *H. zea* and *H. virescens*, based on differing susceptibility to Bt toxin).

The present feeding disruption assay can be tailored for use where species that are difficult to distinguish in the larval stage differ in their susceptibility to a particular pesticide, and where the geographic ranges of the species overlap. The pesticide to be tested is one that disrupts feeding behavior. Sample insects are placed on a test diet containing a predetermined amount of the pesticide and preferably also containing a marker substance. The amount of pesticide in the test diet is sufficient to cause a statistically significant difference in fecal output between resistant and susceptible species over a predetermined time period. The amount of pesticide will vary depending on the pesticide, the insect species, and the time over which feeding is allowed to occur.

Where resistant *H. virescens* are absent from natural populations, the present feeding disruption assay is useful to discriminate between *H. virescens* and *H. zea* larvae, i.e., it is a species discrimination test.

A species-discriminating dose (or 'diagnostic dose') of Bt (determined using the methods described below) is provided in the assay diet, and a test sample of larvae is exposed to the diet for a predetermined time. The rate of feces production is examined over time or at a predetermined time point. The presence of larvae producing a diagnostic amount of feces indicates the presence of *H. zea*. In fields planted with Bt-expressing transgenic crops, the presence of *H. zea* (known to be naturally resistant to Bt) indicates that further pest control measures are necessary.

The production (or lack of production) of blue feces over time at the appropriate diagnostic concentration of Bt is the criterion used to discriminate resistant and non-resistant species.

Where strains of an insect species are known to be resistant to an insecticide, but other strains are susceptible to that insecticide, the present feeding disruption assays are useful in detecting the presence of resistant strains.

A resistance-discriminating dose (or 'discriminating dose') of Bt (determined using the methods described below) is provided in the assay diet, and a test sample of insect is exposed to the diet for a predetermined time. The rate of feces production is examined over time or at a predetermined time point. The presence of insects producing a diagnostic amount of feces indicates the presence of resistant strains. In fields planted with Bt-expressing transgenic crops, the presence of strains resistant to Bt toxin indicates that further pest control measures are necessary.

The production or lack of production of blue feces over time at the appropriate diagnostic concentration of Bt is the criterion used to discriminate resistant and non-resistant species.

As shown in the examples below, Bt resistant YHD2 budworm (*H. virescens*) larvae on test diet containing the appropriate diagnostic dose of Bt and the marker Trypan Blue produce blue feces; susceptible Wake or Wake×YHD2 hybrid *H. virescens* larvae under the same assay conditions produce minimal blue feces. The difference in feces production is sufficient to allow identification of resistant strains.

The present feeding disruption assays are useful in monitoring the development of resistance to a pesticide in natural insect populations.

A resistance-discriminating dose ('discriminating dose') of pesticide (determined using the methods described below) is provided in the assay diet, and a test sample of insects is exposed to the diet for a predetermined time. The production of feces over time is monitored, where a certain level of feces production is indicative of resistance to the insecticide being tested.

The present feeding disruption assays provide a more rapid assessment of resistance than the standard mortality assay. The discriminating dose of insecticide in the test diet determines the minimum detectable level of resistance, and the sensitivity of resistance detection is limited only by population variability in toxicity for susceptible and resistant genotypes. The discriminating dose may be set based on field data of species susceptibility in specific geographical areas, and/or what would be considered economically significant reductions in susceptibility due to selection.

The above resistance monitoring assays are useful in monitoring natural populations of moths for the development of resistance to Bt toxin. Female moths may be collected or trapped in the field and visually identified as to species. Larvae produced by the moths can then be assayed for resistance.

The present feeding disruption assays are useful in assessing different strains within a species for resistance to a pesticide.

A resistance-discriminating dose ('discriminating dose') of pesticide (determined using the methods described below) is provided in the assay diet, and a test sample of insects (of known strains) are exposed to the diet for a predetermined time. The production of feces over time is monitored, where a certain level of feces production is indicative of resistance to the insecticide being tested, and differences among strains in feces production is indicative of differing levels of resistance. The discriminating dose of insecticide in the test diet determines the minimum detectable level of resistance. The discriminating dose may be set based on field data of species susceptibility in specific geographical areas, and/or what would be considered economically significant reductions in susceptibility due to selection.

The above resistance identification assays are useful in identifying insect strains with resistance to an insecticide such as Bt toxin. Strains having known resistance to insecticides are useful in testing new insecticidal formulations.

Apparatus for Conducting the Present Assays

Agar-based insect meals are commonly used in rearing insects. However, agar-based meal-gels require refrigeration, and condensation of water in the cup or syneresis of the gel can create a film of water that immobilizes and/or kills newly emerging larvae. A dry insect diet, hydratable at the time of use with water or with an aqueous solution of insecticide, would be useful in the present feeding disruption assays. Such hydratable meal pads are also useful, when formulated without insecticide, in the routine rearing of insects. Meal pads can also be used for high throughput in vivo screening of chemicals for insecticidal activity where the meal is hydrated at the point of use with an aqueous chemical solution.

A preferred insect meal pad comprises a dry or dehydrated insect meal supported in or on a substrate. The substrate is preferably a porous or water permeable solid or a polymer gel matrix; the insect meal may be coated on the surface of the substrate as a separate layer or contained or embedded within the substrate. Such substrates containing an insect meal are referred to herein as "meal pads", "dehydrated meal pads" or "hydratable meal pads". The meal pads can be stored dry and hydrated with water or with an aqueous solution of insecticide at the time of use.

Existing commercial insect meals, when freshly prepared, are solid-liquid dispersions of insect meal stabilized by agar.

In preparing the present meal pads, solid-liquid preparations of insect meal are cast as films on porous solid substrates or polymer gel matrix substrates and allowed to dry. Alternatively, the solid-liquid dispersion may be impregnated within open porous materials (such as a plastic mesh net) or polymer gel matrices and allowed to dry. The gel matrix support may be a substance that is itself consumable by the insect, for example, a gellable polysaccharide (see U.S. Pat. Nos. 5,141,744; 4,326,052 and 4,326,053; all U.S. patents cited herein are incorporated herein in their entirety). The solid-liquid insect meal may contain agar, low-melting point agarose, or any other lyophilic polymer such as hydroxypropyl cellulose (Klucel) or povidone (PVP).

Beneficial supplements may optionally be added to the meal pads, including fungicides, stabilizers and UV protectants, as are known in the art. Where meal pads are used in the insecticide resistance assays as described herein, a predetermined concentration of insecticide and/or a marker such as Trypan Blue may also be added to the insect meal portion of the meal pad.

Figure 7A:
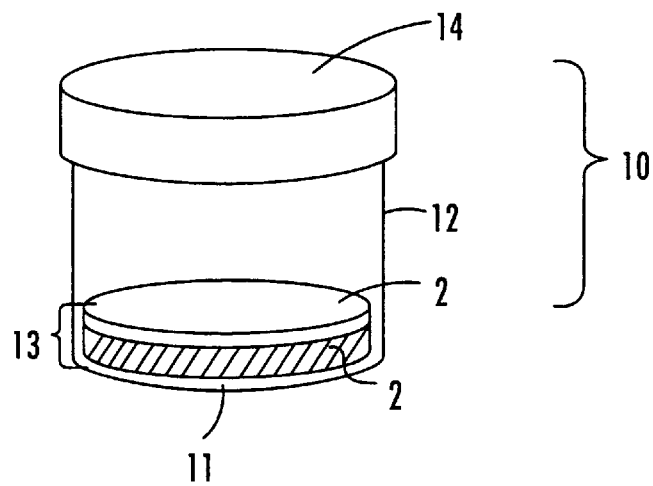
FIG. 7A is a perspective view of apparatus for conducting the feeding disruption assays of the present invention.

As shown in FIGS. 7A*b* and 7B, an apparatus for conducting the feeding disruption assays of the present invention comprises a container 10 for housing insects. The container 10 comprises a floor 11 with sidewalls 12 extending upward from the floor 11 to define an open-topped cavity 13. A removable cap or upper surface 14 is attached to the container 10, so that the open end portion of the container can be closed. The container sidewalls 12 may be essentially perpendicular relative to floor 11, or angled relative thereto; the container 10 may be of any convenient shape including but not limited to cylindrical, cup-shaped and square.

Figure 7B:
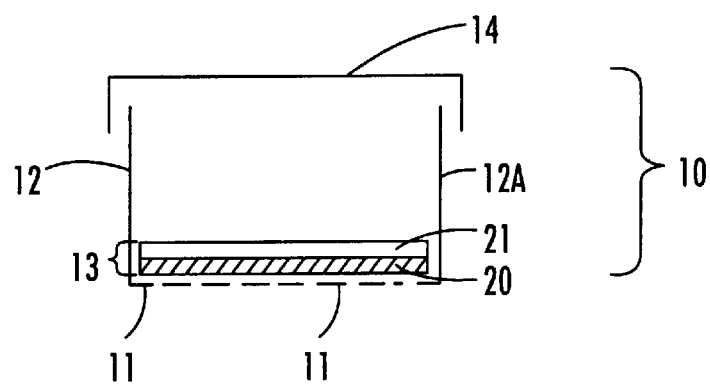
FIG. 7B is a cross-section of apparatus for conducting the feeding disruption assays of the present invention, where the apparatus contains a perforated floor.

Within the container and resting on the floor 11 is an insect-consumable dehydrated (i.e., hydratable) insect meal pad 13. As shown in FIGS. 7A and 7B, the meal pad 13 consists of a porous or mesh substrate layer 20 coated with a layer of dehydrated insect meal 21. The insect meal contains nutritional components suitable to support the particular insect species or genus for which the container is intended. The dehydrated insect meal pad 13 is sized to cover essentially all of the floor 11 within the container; by essentially all it is meant that any gap between the meal pad and container sidewall is small enough that insects housed in the container cannot fit in said gap. The insect meal pad 13 may be formulated to contain a predetermined amount of insecticide within the insect meal layer, and may also contain a marker within the insect meal layer (such as Trypan Blue, discussed above).

Figure 7C:
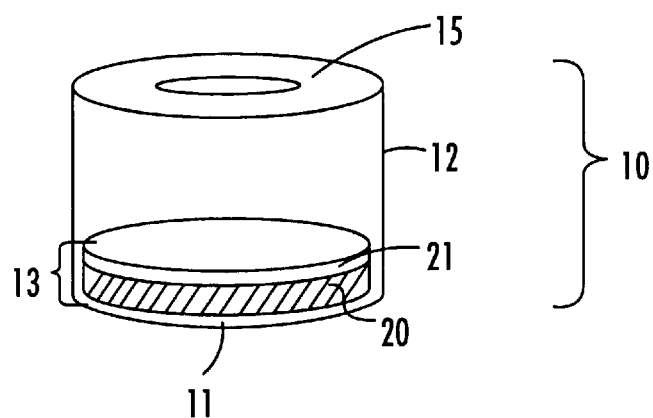
FIG. 7C is a perspective view of apparatus for conducting the feeding disruption assays of the present invention, wherein the ceiling of the container has a hole or aperture formed therein to allow placement of insects within the container.

An alternative embodiment is a container according to FIG. 7A or 7B, but having a ceiling 15 rather than a removable cap 14. The ceiling 15 has formed therein an aperture or hole sized to admit the insect intended to be housed in the container. A still further embodiment is a container according to FIG. 7C, having a ceiling 15 without an aperture formed therein, but having an aperture or hole formed in sidewalls 12.

A further embodiment of the present apparatus is a container having a floor, sidewalls and a ceiling defining an interior space and containing an insect meal pad therein, and having at least one hole or aperture formed in the ceiling or sidewalls of the container. The container is sized according to its intended use, and is of a size suitable to house the insect for which it is intended.

As shown in FIG. 7B, the floor 11 of container 10 may optionally be perforated or foraminated so that the meal pad is in fluid communication with the exterior of the container. The floor 11 may, for example, be formed as or comprise a section that is a grid, latticework or mesh. Alternatively, the floor 11 may be made of a material that is permeable to water, such as cardboard, nitrocellulose or paper. The sidewalls 12 and top surface 14 of the container 10 may be made of the same permeable material as the bottom surface, or of a different (permeable or impermeable) material. The exterior of the floor may optionally include ridges, bumps, extensions or legs, so that when placed on a level surface, the floor 11 is slightly elevated off of an underlying surface. Alternatively, sections of the sidewall(s) may extend downward past the floor 11 so that the floor 11 is slightly elevated from any level surface on which the container 10 is placed. In use, the container 10 is placed in a shallow tray of water so that water passes through the floor 11 to hydrate the meal pad 13 contained therein.

The top surface 14 and/or sidewalls 12 of the container 10 may optionally be perforated to allow the exchange of gases between the container 10 and the outside environment. Preferably the container 10 is made of transparent or semi-opaque material. Suitable materials include, but are not limited to, plastics, silicone, glass, and cardboard. The container 10 may be made of a material that is suitable for re-use (such as silicone), or a disposable material (such as cardboard). The container 10 is sized according to the intended use; a container designed for the *H. zea/H. virescens* species discrimination test as described herein may be a cylindrical container of about ½ inch in height and about ½ inch in diameter.

In use, the hydratable meal pad 13 may be hydrated with any suitable aqueous solution, including solutions containing an appropriate concentration of insecticide useful in a feeding disruption assay according to the present invention.

A plurality of containers 10 may be affixed together, for example in a 4×4 array, 4×6 array, 10×10 array, etc., to provide a unitary multi-chambered apparatus for use in rearing or testing a plurality of insects. The containers are affixed together so that the bottom surfaces of the containers form a plane, i.e., are aligned.

In a further embodiment of the present apparatus, a dehydrated meal pad is placed atop an essentially flat supporting surface. A container such as that of FIGS. 7A or 7B, but lacking a floor 11 or having a perforated or foraminated floor 11 is placed on the meal pad to isolate a test area of the meal pad. A plurality of containers may be placed on the meal pad, or an array of containers affixed together into a unit may be placed on the meal pad. The meal pad is hydrated, either prior to or after placement of the test containers. In a preferred embodiment, the supporting surface that carries the dehydrated meal pad is perforated or formed as a grid, lattice or mesh; in use the supporting surface is placed in an aqueous solution, so that the solution comes in contact with and hydrates the meal pad.

Figure 7D:
FIG. 7D is a perspective view of a meal pad cover suitable for use with the apparatus as shown in FIG. 7A, 7B, or 7C.

In a further embodiment of the present apparatus, an annular meal pad cover 30 is placed atop the meal pad, leaving a central portion of the meal pad exposed and accessible to insect feeding. By exposing only a central area to insect feeding, the majority of feces produced by the insects are deposited on the meal pad cover, and are easily observed. The meal pad cover 30 is essentially flat, and has a diameter essentially equal to that of the meal pad or that of the interior of the container in which it is used (see FIG. 7D). The central opening of the meal pad cover 30 may be of any suitable size, and will vary depending on the insects with which it is used. Preferably the meal pad cover is of a color that contrast with the color of feces produced by the insects being tested, for easy counting and identification. White or light-colored meal pad covers are suitable for use with test diets containing Trypan Blue. Meal pad covers may be made of any suitable material, including but not limited to cardboard, nylon and plastics. The meal pad cover may further contain, be manufactured of, or be coated with a substance that reacts with feces produced by the test insects to produce a mark on the meal pad cover. For example, the meal pad test diet may contain a marker substance that reacts with the meal pad cover to produce a visible mark or chemically detectable reaction on the meal pad cover.

Insects, insect eggs or insect larvae are placed in a container vessel ('test container'), on top of the meal pad enclosed therein. The meal pad is hydrated shortly before or after the placement of insects in the test container. Where the test container has a solid, water-impervious bottom surface, the meal pads are rehydrated by the addition of an aqueous solution to the top of the meal pad. Where the test container has a perforated bottom surface, it can be placed in a shallow tray of water or aqueous solution of insecticide. The meal pad may remain in contact with the aqueous solution during use to maintain hydration of the meal pad. The hydrating solution may contain a predetermined concentration of insecticide (e.g., a diagnostic dose of an insecticide for use in a resistance assay), or the meal pads may be formulated to contain a predetermined dose of insecticide.

The examples which follow are set forth to illustrate the present invention, and are not to be construed as limiting thereof.

EXAMPLE 1

Materials and Methods

Insects were reared in the laboratory at 27±1° C. with a 14:10 (light:dark) cycle on a standard artificial diet (Gould et al., 1995; Rose et al., 1995). The Wake strain of *H. virescens* used was originally collected in 1986 from tobacco in Wake county, N.C. The YHD2 strain was originally collected as eggs from seven tobacco fields in Yadkin County, N.C., in July of 1988. The YHD2 larvae were reared each generation for about seven days from egg hatch on 1000 µg of Bt toxin CryIAc (MVP, commercial grade, >98.0% δ endotoxin, Mycogen Corporation, San Diego) per ml of artificial diet and then transferred to insecticide-free diet for the remainder of development. The YHD2 strain is >2000-fold resistant to CryIAc, compared to the Wake strain (Gould et al., *J. Econ. Entomol.* 88:1545 (1995)).

During the course of these studies, the Bt toxin LC50s for the YHD2 and Wake strains were 2952 (95% confidence interval, 2247–3604; slope 3.23) and 0.0017 (0.0002–0.0038; 1.03) µg CryIAc/ml diet, respectively, using a seven day mortality assay on neonates. Mortality data were analyzed using probit analysis (PROC PROBIT, SAS 1991). Based on the low LC50 for Wake tobacco budworms versus that for YHD2, the Wake strain is designated as Bt susceptible.

Hybrid F1 larvae were obtained for testing from a YHD2 (female)×Wake(male) cross with 100 insects from each strain. This cross was duplicated and studies conducted with the F1 generation from each duplicate. The LC50 was 0.129 (95% confidence interval, 0.091–0.178; slope 3.19) µg CryIAc/ml diet in the hybrid larvae.

In addition to testing larvae from artificial diet, Wake and YHD2 larvae were reared from egg hatch through the third stadium on cotton plants, *Gossypium barbardense* (variety "Delta Pine Nutty"), in the greenhouse at 25° C. during the day and 18° C. at night (12:12, light:dark). Plants containing different strains were isolated by a distance of 10 meters to prevent cross-contamination. *H. zea* were obtained from cotton plants in Plymouth, N.C. in August and September of 1996 and reared in the laboratory on the same artificial diet as that used for *H. virescens*.

EXAMPLE 2

Feeding Disruption Assay

The blue diet used in the feeding disruption bioassay is an agar based insect meal containing 20 mg of Trypan Blue (Direct Blue 14; Matheson Coleman & Bell, Norwood, Ohio) per 100 ml of standard artificial diet, and containing different concentrations of CryIAc (MVP, Mycogen). Larvae feeding on this colored diet produced blue feces which were easily distinguished by observation from feces derived from other food sources. Assays were conducted in 1-ounce clear plastic cups (Solo Cup Company, Urbana, Ill.; approximately ½ inch in diameter and ¾ inches high) fitted with white cardboard tops, which are routinely used for insect rearing in our laboratories. The clear plastic allowed for the observation of blue feces without opening the container.

Third instars from Wake (Bt susceptible), YHD2 (Bt resistant), and YHD2×Wake hybrid strains of the tobacco budworm (*H. virescens*) were used. Instars weighed 30±5 mg and were reared either on standard artificial diet or cotton plants. Instars were starved for one hour and then transferred to clear plastic assay cups, one larvae per cup. The starvation treatment synchronized the beginning of feeding between individuals once transferred to the dye-containing diet. The effect of different concentrations of CryIAc (0 to 0.064 µg CryIAc/ml diet) on the production of blue feces was examined for one to 24 hours at 27±1° C. and 16: (light:dark). Studies were conducted in triplicate with 15 larvae per replicate. Once a diagnostic concentration and optimum assay time were identified from these experiments, the accuracy of resistance detection was investigated for individual resistant and susceptible neonates of *H. virescens*. These experiments were duplicated for 25 resistant and 25 susceptible budworms from two different budworm generations.

The diagnostic concentration for resistance detection was also investigated for its ability to distinguish Wake susceptible *H. virescens* from *H. zea*. In addition, dose response studies were conducted to identify a concentration of Bt that would distinguish resistant YHD2 neonates of *H. virescens* from *H. zea*. Dose response studies were duplicated for 25 resistant (HD2) tobacco budworms and 25 bollworms from two generations at different doses of Bt ranging from 0 to 1000 µg CryIAc/ml of blue diet.

EXAMPLE 3

Effects of Trypan Blue on Feeding

The rate of feces production was examined for third instars of both the Wake (Bt susceptible) and YHD2 (Bt resistant) strains of *H. virescens*, to examine the effects of adding Trypan Blue to the standard artificial diet (the "Blue diet"). Wake budworms produced 30.6 (90.5% confidence interval, 27.6–33.6) fecal pellets/hour/15 larvae on regular diet, and 25.5 (22.5–28.5) fecal pellets/hour/15 larvae on Trypan Blue diet. This difference, although small, was statistically significant as indicated by a significant diet×time interaction (F=6.05; df=1,24; P=0.0215) (PROC GLM procedure, SAS 1991). (Data not shown).

In contrast, the rate of fecal pellet production by the YHD2 strain did not differ between the regular and Trypan Blue diets, as indicated by the lack of a significant diet main effect (F+0.13; df=1,18; P=0.7248) and the lack of a significant diet×time interaction effect (F=0.08; df=1,8; P=0.7834) in an analysis of variance. The rates of fecal pellet production by YHD2 third instars were 34.4 (31.6–37.2) fecal pellets per hour per 15 larvae on the regular diet, and 34.9 (32.5–37.3) on the Trypan Blue diet. The YHD2 strain had a significantly higher feces production rate on Blue diet than the Wake strain (strain×time interaction significant; F=19.62; df=1,24; P=0.002). The difference, however, is small relative to the inhibitory effects of Bt on feces production and does not preclude the use of Trypan Blue as a feeding indicator in the bioassay. (Data not shown).

EXAMPLE 4

Resistance Assay on Homogenous Populations

FIG. 1 shows the rates of production of blue feces by susceptible (Wake), and resistant (YHD2), and hybrid (YHD2 (female)×Wake(male)) third instars of *H. virescens* on Trypan Blue diet containing different concentrations of Bt toxin CryIAc. Each test was conducted in triplicate on 15 third instars per replicate. Although both susceptible (Wake) and resistant (YHD2) budworms produced blue feces in these studies, relatively little blue feces was produced through 24 hours by the susceptible budworms as compared to the resistant YHD2 strain. For example, after 24 hours at 0.032 μg of CryIAc/ml of diet, susceptible (Wake) budworms produced a total of 12 fecal pellets/15 larvae (0.8/larva) as compared to 470 (31/larva) for resistant (YHD2) larvae. FIG. 1. Even at 24 hours for concentrations as low as 0.008 μg/ml, fecal production was extremely low in the susceptible budworms (63, 4/larva) as compared to the resistant YHD2 strain (800, 53/larva).

These results indicate that a bioassay time of at least about four hours is needed to effectively discriminate between the resistant (YHD2) and susceptible (Wake) budworm populations at toxin concentrations of 0.008 to 0.064 μg/ml in these experiments. However, at least about 0.032 μg of CryIAc/ml blue diet appeared to be preferable as a diagnostic concentration for distinguishing resistant (YHD2) from susceptible (Wake) budworms since blue fecal production was minimal in the susceptible budworms at this concentration. Only 1.6 (0.1/larva), 5 (0.3/larva) and 12 (0.8/larva) blue fecal pellets were produced by susceptible larvae at 4, 8 and 24 hours as compared to 46 (3/larva), 129 (9/larva) and 470 (31/larva), respectively, for resistant budworms.

The detection of resistance in heterozygotes with a much lower LC50 than that of the YHD2 strain was also possible, although differences between the F1 hybrids and Wake larvae were not as distinct as those between YHD2 and Wake. The rate of fecal production in the YHD2×Wake hybrids was intermediate between that of YHD2 and Wake at all of the concentrations of CryIAc tested (FIG. 1). Because the overall production rate of blue feces was greatly reduced in the F1 hybrids as compared to the YHD2 strain, a bioassay time of about 24 hours was needed for a firm diagnosis. In these studies, a successful diagnosis of the hybrid was possible at concentrations ranging from 0.004 to 0.032 μg of CryIAc/ml of diet (FIG. 1). The 0.032 μg/ml dose at 24 hours produced 470 fecal pellets (31/larva) for the YHD2 strain, 68 (5/larva) for the hybrid and 12 (0.8/larva) for the Wake susceptibles. A single diagnostic concentration of 0.032 μg/ml can distinguish the Wake strain (LD50=0.0017 μg CryIAc/ml diet) from the highly resistant YHD2 strain (LD50=2952.0) after a minimum of about four hours and the YHD2×Wake hybrid (LD50=0.129) after 24 hours.

In the present assays, differing resistance levels can be detected by simply changing the duration of the bioassay time from 4 to 24 hours.

EXAMPLE 5

Resistance Assay in Cotton-fed Larvae

The previous experiments were conducted on budworms reared exclusively on artificial diet. To examine whether plant reared, resistant (YHD2) and susceptible (Wake) tobacco budworms could be distinguished with this method, neonates from both strains were reared to the third stadium on cotton plants in the greenhouse and then assayed for resistance using the feeding disruption assay.

At a concentration of 0.032 μg of CryIAc/ml of Blue diet, our assay discriminated between the Wake and YHD2 populations reared on cotton (FIG. 2) similar to insects raised on artificial diet (FIG. 1). Essentially no blue feces were produced by the susceptible insects from cotton while at 24 hours, >140 fecal pellets were produced per 15 larvae by the YHD2 strain.

Figure 3:
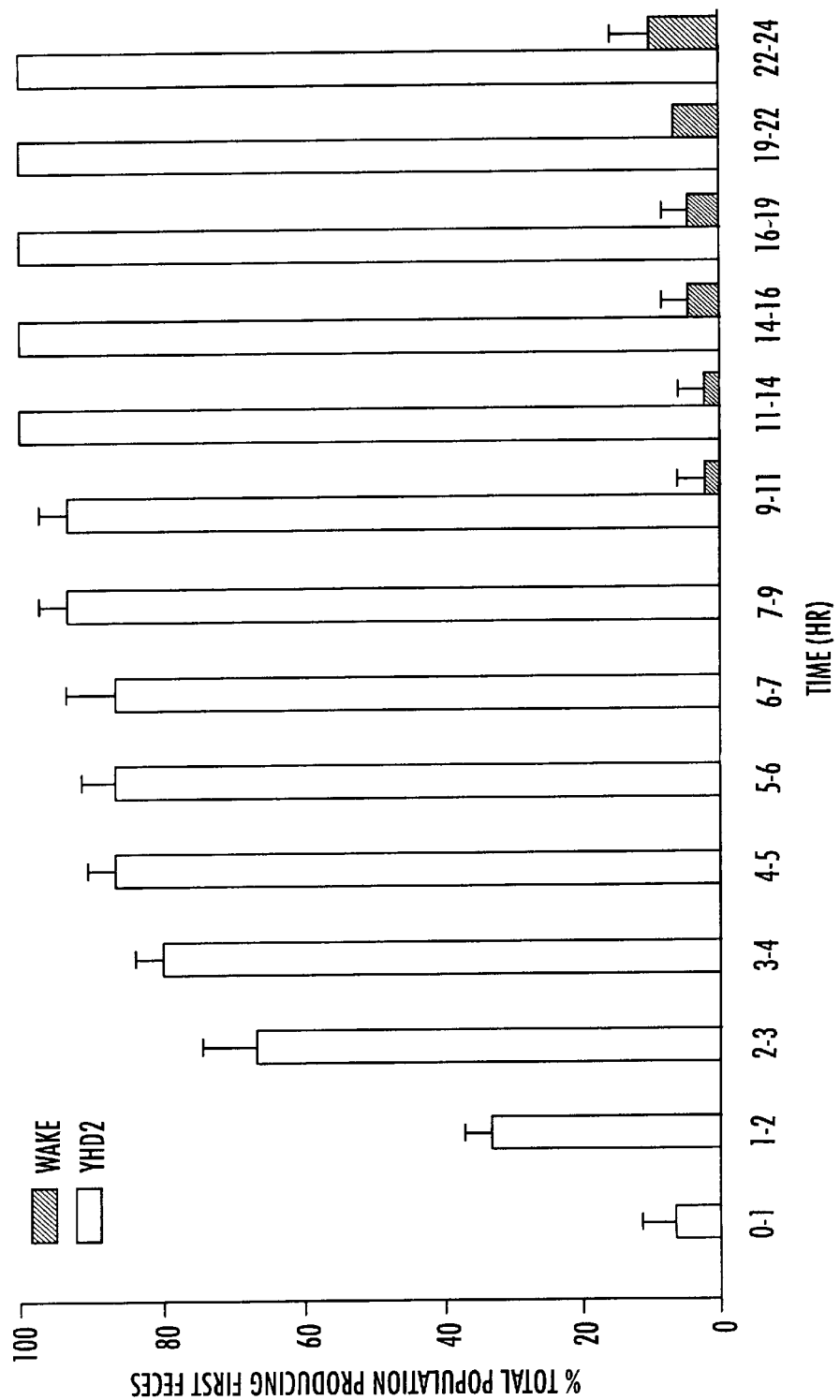
FIG. 3 graphs the percentage of the total population of Wake (shaded bars) versus YHD2 (open bars) third instars producing the first blue fecal pellet at different time intervals after the larvae were transferred to the surface of the CryIAc-Trypan Blue diet (0.032 μg CryIAc/ml). Each treatment is the average of three replicates of 15 insects per replicate. Error bars are ±1 S.E., which in most cases does not exceed the size of the graph symbol.
Figure 5A:
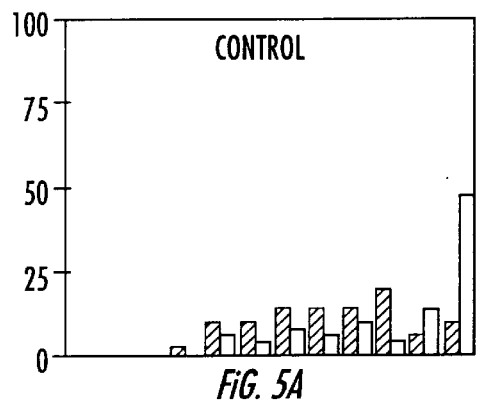
FIG. 5A graphs the percentage of the test population of YHD2 (shaded bars) and *Helicoverpa zea* (open bars) neonates producing blue fecal pellets over 24 hours on Trypan Blue diet containing no CryIAc toxin. The results were taken from two replicates of 25 insects per replicate for each species.
Figure 5B:
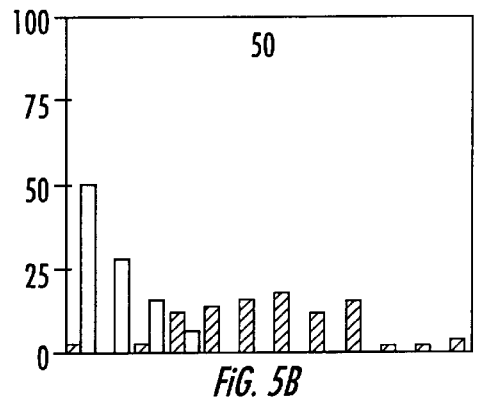
FIG. 5B graphs the percentage of the test population of YHD2 (shaded bars) and *Helicoverpa zea* (open bars) neonates producing blue fecal pellets over 24 hours on Trypan Blue diet containing 50 μg CryIAc/ml diet. The results were taken from two replicates of 25 insects per replicate for each species.
Figure 5C:
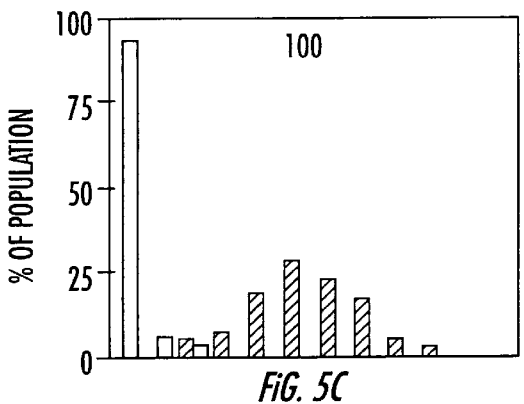
FIG. 5C graphs the percentage of the test population of YHD2 (shaded bars) and *Helicoverpa zea* (open bars) neonates producing blue fecal pellets over 24 hours on Trypan Blue diet containing 100 μg CryIAc/ml diet. The results were taken from two replicates of 25 insects per replicate for each species.
Figure 5D:
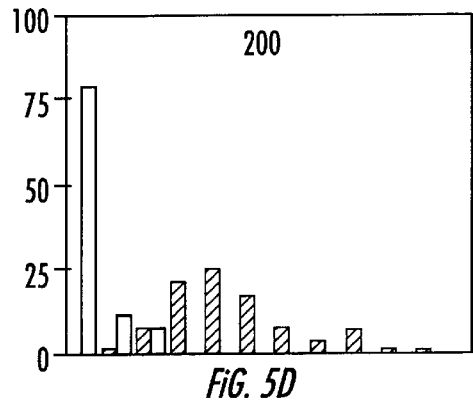
FIG. 5D graphs the percentage of the test population of YHD2 (shaded bars) and *Helicoverpa zea* (open bars) neonates producing blue fecal pellets over 24 hours on Trypan Blue diet containing 200 μg CryIAc/ml diet. The results were taken from two replicates of 25 insects per replicate for each species.
Figure 5E:
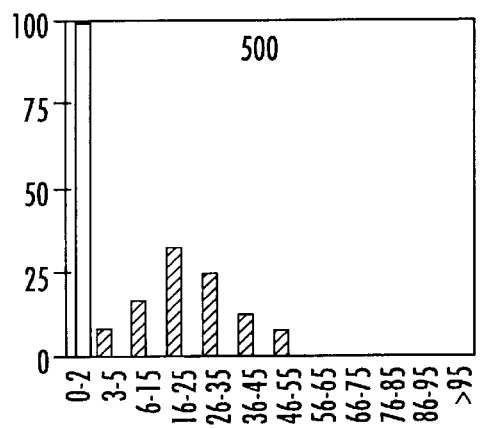
FIG. 5E graphs the percentage of the test population of YHD2 (shaded bars) and *Helicoverpa zea* (open bars) neonates producing blue fecal pellets over 24 hours on Trypan Blue diet containing 500 μg CryIAc/ml diet. The results were taken from two replicates of 25 insects per replicate for each species.
Figure 5F:
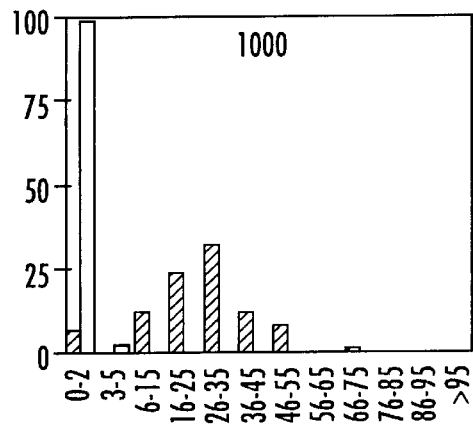
FIG. 5F graphs the percentage of the test population of YHD2 (shaded bars) and *Helicoverpa zea* (open bars) neonates producing blue fecal pellets over 24 hours on Trypan Blue diet containing 1000 μg CryIAc/ml diet. The results were taken from two replicates of 25 insects per replicate for each species.

At a diagnostic concentration of 0.032 μg CryIAc/ml, 85±3.9 (1 S.E.)% of the resistant (YHD2) *H. virescens* produced one or more blue fecal pellets in 5 hours; 95±3.9% produced one or more blue fecal pellets in 9 hours, and 100.0±0.0% produced one or more blue fecal pellets in 14 hours (FIG. 3). The delay in fecal production by some resistant budworms is likely due to developmental differences at the beginning of the assay. By simply looking for the presence of blue fecal material and classifying larvae as resistant if blue fecal pellets were present, or susceptible if blue fecal pellets were absent, 95% of the YHD2 budworms could be accurately classified as resistant, and all of the Wake larvae could be accurately classified as susceptible after 9 hours. After 14 hours, 100% of the resistant insects could be correctly classified, but 2.2±3.9% of the Wake larvae had produced blue feces and would be incorrectly classified as resistant (FIG. 3). The initial classification of larvae as resistant could be verified by counting blue fecal pellets after 24 hours or by examining mortality a few days later.

These results establish that resistant and susceptible strains of plant-reared budworms can be distinguished using the present feeding disruption assay, and that insects reared on artificial diets can represent plant-reared insects in assessing feeding disruption assays.

EXAMPLE 6

Species and Resistance Diagnosis in Individual Insects

The above examples using third instars demonstrate the feasibility of using fecal production as an indicator of resistance to Bt toxins in the tobacco budworm. However, eggs are the easiest stage to collect from the field, and can be hatched by growers to provide neonatal larvae for resistance testing so that results are obtained early enough for corrective management. Additionally, in field samples, the populations will not necessarily be homogenous with respect to Bt susceptibility or species composition. Natural pest populations in cotton today include Bt susceptible *H. virescens* and Bt resistant *H. zea*.

Using the Blue diet described above and containing a discriminating concentration of 0.032 μg CryIAc/ml diet, and a 24 hour feeding time followed by a single observation, the present feeding disruption assay distinguished neonates of susceptible (Wake) tobacco budworm from the resistant bollworm with 100% accuracy (FIG. 4). Insects producing six or fewer fecal pellets were *H. virescens* and larvae producing ≧7 blue fecal pellets were *H. Zea*. FIG. 4. Only 1 out of 50 *H. virescens* produced six blue fecal pellets and 99% of *H. zea* produced ≧15 blue fecal pellets. The difference in fecal production between neonates of *H. virescens* and *H. zea* is greatly increased by waiting an additional 12 to 24 hours; during this time the budworms produced no additional fecal pellets. Additional characteristics that distinguished susceptible *H. virescens* budworms from resistant *H. zea* bollworms were apparent at 24 hours: *H. zea* larvae were noticeably larger at 24 hours, and most *H. zea* larvae maintained contact with the diet while the susceptible *H. virescens* larvae were physically away from the diet. In addition, mortality can be determined as a final check after 3–7 days.

EXAMPLE 7

Distinguishing Among Resistant Insects

Although the 0.032 μg CryIAc/ml diet was suitable to distinguish resistant from susceptible neonates of *H. virescens* at 24 hours, this concentration did not adequately distinguish the highly resistant *H. virescens* strain from *H. zea* (FIG. 4). Additional dose/response studies were conducted to determine a diagnostic concentration that would distinguish resistant YHD2 neonates from resistant *H. zea*. As shown in FIG. 5, using 500 μg CryIAc/ml in blue diet allowed discrimination of resistant YHD2 neonates from *H. zea*.

Using 500 μg CryIAc/ml in blue diet, 100% of *H. zea* produced no blue feces and the minimum fecal production by any individual YHD2 tested was five fecal pellets. As the Bt concentration approached zero, or was increased to 1000 μg/ml, the separation between species was not complete (FIG. 5). As discussed above, discrimination increased with assay time, and additional behavioral and developmental criteria exist that facilitate a correct diagnosis.

The above studies demonstrate that for susceptible *H. virescens* and *H. zea* and highly resistant laboratory *H. virescens* (YHD2), the present feeding disruption assay can effectively diagnose the presence of resistant species and resistance in individual insects. For use in field populations, assessment of regional variations in baseline levels of budworm and bollworm susceptibility to Bt, and potentially different levels of Bt resistance, will be useful to tailor the feeding disruption assay to particular regions. Studies of geographically diverse field populations of *H. virescens* and *H. zea* are conducted as needed to examine these questions and determine appropriate diagnostic doses.

EXAMPLE 8

Feeding Disruption Assay to Assess Resistance to a Carbamate Insecticide

The feeding disruption assay described above can also be used to detect resistance to chemical insecticides. *H. virescens* resistance to a carbamate insecticide was achieved by substituting a diagnostic dose of LARVIN® (thiodicarb; Rhone Poulenc Ag Co., Research Triangle Park, N.C.) for the Bt used in the preceding examples.

Figure 6:
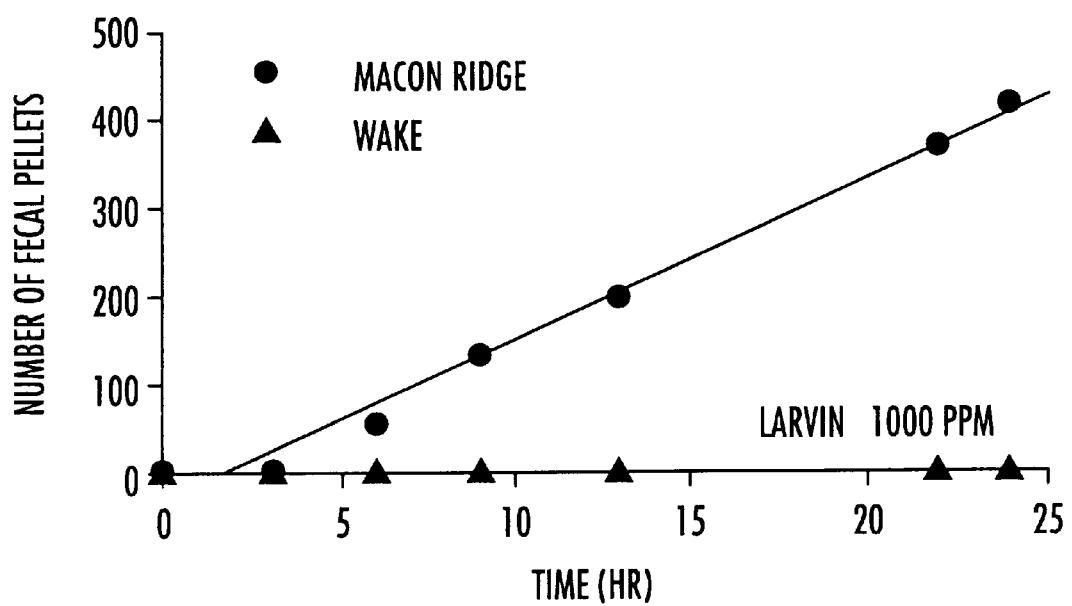
FIG. 6 graphs the number of fecal pellets produced over time by two strains of *H. virescens* exposed to a test diet containing a carbamate insecticide (LARVIN®). One strain (Macon Ridge; closed circles) was resistant to the insecticide; the other strain (Wake; closed triangles) was susceptible.

Two strains of *H. virescens* were utilized. The Wake strain was known to be susceptible to thiodicarb; the Macon Ridge strain was known to be resistant to thiodicarb. LARVIN® was added to a test diet at 1000 ppm and the larvae were allowed to feed; FIG. 6 graphs the production of fecal pellets over time. As shown in FIG. 6, the resistant and susceptible strains can be distinguished within hours based on fecal pellet production.

EXAMPLE 9

Field Studies

The eggs and young larvae of *H. zea* and *H. virescens* are indistinguishable by simple observation in the field. Neonate larvae were collected from fields in Plymouth and Rocky Mount, N.C., and 110 larvae were assessed using a feeding disruption assay containing 0.032 μg/ml of Bt over 48 hours. The larvae were successfully diagnosed as either *H. zea* (82 larvae) or *H. virescens* (28 larvae) (data not shown).

The foregoing examples are illustrative of the present invention, and are not to be construed as limiting thereof. The invention is described by the following claims, with equivalents of the claims to be included therein.

That which is claimed is:

1. A method of detecting, in a plurality of insect larvae with the visual appearance of *H. virescens* larvae, the presence of *H. zea* larvae, comprising:
  a) giving each of said larvae access to a test diet containing a predetermined diagnostic amount of *Bacillus thuringiensis* toxin, for a predetermined time; and then
  b) counting the amount of feces produced by each of said larvae over said predetermined time;
wherein any larva producing more than a predetermined diagnostic amount of feces are *H. zea*.

2. A method according to claim 1, wherein said test diet further comprises a marker compound that imparts a detectable characteristic to feces.

3. A method according to claim 1, wherein said test diet further comprises Trypan Blue.

4. A method according to claim 1 wherein said diet contains CryIAc *Bacillus thuringiensis* toxin at a concentration of from about 0.030 μg to about 0.035 μg CryIAc/ml diet, said predetermined time is 24 hours, and a larva producing seven or more fecal pellets is *H. zea*.

5. A method according to claim 1, further comprising the step of starving said larvae for a predetermined period of time prior to step (a).

6. A method of detecting, in a plurality of insects, the presence of insects resistant to a pesticide that causes feeding disruption in susceptible insects, comprising:
  a) giving each of said insects access to a test diet containing a predetermined diagnostic amount of said insecticide, for a predetermined time; and then
  b) quantifying the amount of feces produced by each of said insects over said predetermined time;
wherein an insect producing more than a predetermined diagnostic amount of feces is resistant to said pesticide.

7. A method according to claim 6, wherein said test diet further comprises a marker compound that imparts a detectable characteristic to feces.

8. A method according to claim 6, wherein said test diet further comprises Trypan Blue.

9. A method according to claim 6, wherein said plurality of insects comprises *Helicoverpa zea* larvae and *Heliothis virescens* larvae.

10. A method according to claim 6, wherein said pesticide is selected from *Bacillus thuringiensis* toxins and carbamate pesticides.

11. A method according to claim 6, wherein said pesticide is *B. thuringiensis* toxin and said plurality of insects comprises larvae selected from the group consisting of *H. virescens* and *H. zea* larvae.

12. A method according to claim 6, wherein said insects resistant to the pesticide are *H. zea*.

13. A method according to claim 6, wherein said pesticide is a carbamate pesticide and said population of insects comprises *H. virescens* larvae.

14. A method according to claim 6, further comprising the step of starving said insects for a predetermined period of time prior to step (a).

15. A method of assessing insects for resistance to a pesticide that causes feeding disruption in susceptible insects, comprising:
   a) giving said insects access to a test diet containing a predetermined diagnostic amount of said insecticide, for a predetermined time; and then
   b) counting the amount of feces produced by said insects over said predetermined time;
wherein production of more than a predetermined diagnostic amount of feces indicates that said insect is resistant to said pesticide.

16. A method of designing an assay to discriminate between an insect type resistant to a pesticide and an insect type susceptible to a pesticide, where said pesticide causes feeding disruption, comprising:
   a) obtaining a plurality of each of said insect types;
   b) conducting a dose/response study of said pesticide in a test diet, to determine a diagnostic dose of said pesticide and a diagnostic feeding period sufficient to distinguish, by number of feces produced during the feeding period, said resistant insect type from said susceptible insect type.

17. A method of designing an assay to screen for the development of pesticide resistance in a homogenous population of insects, where said pesticide causes feeding disruption, comprising:
   a) obtaining a plurality of insects from said population of insects;
   b) conducting a dose/response study of said pesticide in a test diet to determine a diagnostic dose of said pesticide and a diagnostic feeding period at which a statistically significant decrease in the number of feces produced by said insects occurs, compared to fecal production by insects on a control diet.

* * * * *